United States Patent [19]

Harris, Jr.

[11] 4,294,955
[45] Oct. 13, 1981

[54] POLYMERS FROM PHENYLTEREPHTHALIC ACID

[75] Inventor: John F. Harris, Jr., Wilmington, Del.

[73] Assignee: E. I. Du Pont de Nemours and Company, Wilmington, Del.

[21] Appl. No.: 102,040

[22] Filed: Dec. 10, 1979

[51] Int. Cl.³ .............................................. C08G 63/18
[52] U.S. Cl. ................. 528/176; 264/176 F; 528/190; 528/193; 528/194
[58] Field of Search ................ 528/176, 190, 193, 194

[56] References Cited

U.S. PATENT DOCUMENTS

| | | | |
|---|---|---|---|
| 3,160,603 | 12/1964 | Holub | 528/191 |
| 3,723,388 | 3/1973 | Bell et al. | 528/193 |
| 4,065,432 | 12/1977 | Frazer | 264/176 F X |
| 4,118,372 | 10/1978 | Schaefgen | 528/191 |
| 4,153,779 | 5/1979 | Jackson, Jr. et al. | 528/193 |
| 4,156,070 | 5/1979 | Jackson, Jr. et al. | 528/191 X |
| 4,156,070 | 5/1979 | Jackson, Jr. et al. | 528/193 |
| 4,159,365 | 6/1979 | Payet | 528/176 X |
| 4,183,895 | 1/1980 | Luise | 528/191 |

FOREIGN PATENT DOCUMENTS

| | | |
|---|---|---|
| WO79/01034 | 11/1979 | Int.'l Appl. |
| 885739 | 12/1961 | United Kingdom |
| 993272 | 5/1965 | United Kingdom |

OTHER PUBLICATIONS

Chem. Abstracts, vol. 49, (1954), 5396g, from Annalen 586, 138–146 (1954).

Primary Examiner—Howard E. Schain

[57] ABSTRACT

Melt-spinnable anisotropic-melt-forming aromatic polyesters are prepared from phenylterephthalic acid or mixtures thereof with one or more selected aromatic dicarboxylic acids and one or more selected aromatic diols. The tenacity of as-spun filaments from these polyesters can be increased by heat treatment.

7 Claims, No Drawings

POLYMERS FROM PHENYLTEREPHTHALIC ACID

TECHNICAL FIELD

This invention relates to fiber-forming, melt-spinnable aromatic polyesters and to filaments therefrom.

BACKGROUND

Melt-spinnable, aromatic polyesters prepared from aromatic diols and mono-substituted terephthalic acids wherein the substitutents include Br, Cl, alkyl of 1-3 carbon atoms and alkoxyl are known (U.S. Pat. Nos. 4,065,432, 4,156,070; U.K. No. 993,272). Polyesters containing phenyl-substituted isophthalic acid are disclosed in U.K. No. 885,739.

Melt-spinnable, fiber-forming polyesters capable of forming optically anisotropic melts, prepared from monophenylhydroquinone and terephthalic acid, are disclosed in U.S. Pat. No. 4,159,365.

Phenylterephthalic acid is known (Annalen 586, 138-46 (1954)).

The art is confusing on the relative effects of substituents on the diacid and diol components of aromatic polyesters. U.S. Pat. No. 4,118,372 teaches that, in the preparation of aromatic, melt-spinnable polyesters capable of forming optically anisotropic melts, it is preferable that the diol be substituted with halogen or lower alkyl and that the diacid remain unsubstituted because of thermal or hydrolylic instability and/or cost of copolymers prepared from ring-substituted aromatic diacids. U.S. Pat. No. 3,160,603 teaches that aromatic, fiber-forming, initially amorphous polyesters in which the diacid is chloro-substituted show much less tendency to crystallize than isomeric polyesters wherein the diol is chloro-substituted. U.K. No. 993,272 discloses unexpectedly crystalline polyesters prepared from (asymmetric) monoethyl-, alkoxyl- or chloro-substituted terephthalic acid and like-substituted hydroquinone. A substantial amount of an unsubstituted third reactant (diacid or diol) may be incorporated while retaining crystallinity.

SUMMARY OF THE INVENTION

This invention provides melt-spinnable, fiber-forming (co)polyesters that are optically anisotropic in the melt and which consist essentially of recurring units having the structural formulas

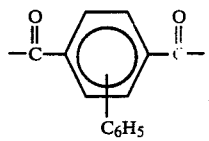   (1)

or a combination of (1) and up to 50 mol % of

   (2)

wherein $R^1$ is 1,4-phenylene, 2,6-naphthalene, 4,4'-biphenylene or mixtures thereof and (3) —O—$R^2$—O— wherein $R^2$ is 1,4-phenylene, 2,6-naphthalene, 1,4-naphthalene, 4,4'-biphenylene or mixtures thereof or a combination of (3) with up to 20 mol % of

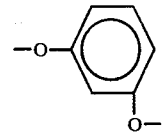

based on the total mols of dioxy units present. The recurring units (1), or a combination of (1) and (2) are present in substantially equimolar amounts with recurring dioxy units.

The (co)polyesters of this invention may be prepared by standard melt-polymerization techniques from the appropriate aromatic dicarboxylic acids and dihydric phenols that provide the units described above. Thus, phenylterephthalic acid may be employed as the sole acid reactant or it may be combined with one or more diacids selected from the group consisting of terephthalic acid, 2,6-naphthalene dicarboxylic acid and 4,4'-bibenzoic acid, in such amounts that the phenylterephthalic acid constitutes at least 50 mol % of the acid mixture. The dihydric phenol reactant(s) is selected from the group consisting of hydroquinone, 1,4-naphthalene diol, 2,6-naphthalene diol, and 4,4'-biphenol. Resorcinol may be employed in addition to one or more of the aforementioned dihydric phenols in an amount of up to 20 mol % based on the total mols of dihydric phenol reactant. It is ordinarily preferred to employ the diols in the form of diesters because said esters can usually be prepared in higher purity, of importance in the preparation of high molecular weight polyesters.

Diols or diesters, preferably diesters, most preferably diacetates, and diacids are normally combined in substantially equimolar amounts and heated in a stirred reaction vessel in an inert atmosphere, e.g., under nitrogen or in vacuum, with stirring for about 30 minutes to 36 hours. A stoichiometric excess of either diacid or diol (diester) of up to 10 mol % may be used without detriment. Temperatures employed for the polymerization are above the melting points of the reactants and are generally in the range of about 200° to about 350° C. The reaction vessel is equipped with a means to permit by-product removal during polymerization; for example a combined distillation head-condenser.

Reaction is generally initiated at about 200° to 220° C. and the temperature is gradually raised in stages as polymerization proceeds. Towards the end of the polymerization, the molten polymer may be placed under reduced pressure and heated further to complete the by-product removal and the polymerization. Optionally, the molten polymer may be transferred directly to an appropriate apparatus for preparation of shaped articles, e.g., a fiber spinning unit. Polymerization conditions such as temperature, duration of heating, pressures and the like, may be varied according to the reactants employed and the degree of polymerization desired.

In an alternative, but less preferred procedure, both the diacids and diols may be employed in the form of diesters. In such cases a catalyst such as dibutyl tin oxide may be desirable.

DETAILED DESCRIPTION OF THE INVENTION (Co)polyesters of this invention have molecular weights and melting points sufficient for melt-spinning into filaments.

A preferred polyester composition of this invention,

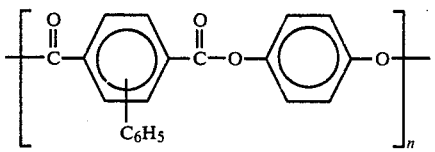

prepared from phenylterephthalic acid and hydroquinone, differs from a prior art polyester disclosed in U.S. Pat. No. 4,159,365 wherein the phenyl substituent is located on the diol segment; i.e.,

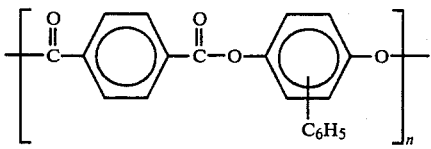

As is shown in Example 1C, the polymer of this invention, surprisingly is significantly lower melting that the art polymer, a definite economic advantage in the melt processing of polyesters.

FILAMENT PREPARATION

The preferred (co)polyesters of this invention may be spun into filaments, by conventional melt-spinning techniques. A melt of the polymer is extruded through a spinneret into a quenching atmosphere (e.g., air or nitrogen maintained at room temperature) and wound up. General spinning conditions are given in U.S. Pat. No. 4,066,620.

As used herein, the term "as-spun" fiber refers to a fiber which has not been drawn or heat treated after extrusion and normal windup.

HEAT TREATMENT AND UTILITY

The as-spun fibers of this invention may be subjected to heat treatment in an oven while relaxed to provide high strength fibers useful for a variety of industrial applications such as plastic and rubber reinforcement. In the heat treating process, fiber samples, as skeins or on bobbins (preferably collapsible bobbins) are usually heated in an inert atmosphere that is continuously purged by flow of inert gas such as nitrogen through the oven to remove by-products from the vicinity of the fiber. Temperatures approaching the fusion point but sufficiently below to prevent interfilament fusion are employed. Preferably the maximum temperature is reached in a stepwise fashion.

MEASUREMENTS AND TESTS

Inherent Viscosity ($\eta_{inh}$) is defined by the equation $$\eta_{inh} = \frac{\ln(\eta_{rel})}{C}$$

wherein ($\eta_{rel}$) represents the relative viscosity and C represents a concentration of 0.25 gram of the polymer in 100 ml of solvent. The relative viscosity ($\eta_{rel}$) is determined by dividing the flow time in a capillary viscometer of the dilute solution by the flow time for the pure solvent. Flow times are determined at 25° C., and the solvent is hexafluoroisopropanol unless otherwise indicated.

Fiber tensile properties are reported as follows:

| | |
|---|---|
| Denier | in g/9000m (dtex) |
| Tensile Strength (Tenacity) | in g/denier (dN/tex) |
| Elongation | in percent of unstretched length |
| Intitial Modulus | in g/denier (dN/tex) |

They are measured using the procedures shown in Morgan U.S. Pat. No. 3,827,998 on fibers that have been conditioned for at least one hour. At least three breaks are averaged.

The Thermooptical Test (TOT), which involves heating a polymer sample between crossed (90°) polarizers on the heating stage of a polarizing microscope, is fully described in U.S. Pat. No. 4,066,620. Polymers that pass this test (+) are considered to be optically anisotropic in the molten state. Polymers which do not pass the TOT (−) are considered to be optically isotropic in the molten state.

The melting behavior and fiber-forming capability of polyesters of this invention were determined by heating a sample of the polymer on a metal block, as described in the ensuing examples which are illustrative of the present invention. The polymer flow temperature was determined on the hot stage polarizing microscope.

The term "consisting essentially of" is intended to have its customary meaning; namely, that all specified materials and conditions are very important in practicing the invention but that unspecified materials and conditions are not excluded so long as they do not prevent the benefits of the invention from being realized.

EXAMPLE 1

A. Polyester of Phenylterephthalic Acid and Hydroquinone Diacetate

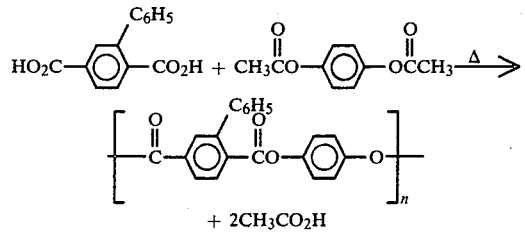

All equipment was dried in an oven at 135° C. and allowed to cool in a nitrogen atmosphere. In a 100-ml flask was placed 6.00 g of phenylterephthalic acid and 4.81 g of hydroquinone diacetate. The flask was fitted with 15 cm extension tube and a short path still head which had a small paddle stirrer inserted into it reaching to the bottom of the reactor and a small round bottomed flask as receiver. The assembled set-up was connected to a nitrogen bubbler and then the mixture was heated in an oil bath, stirred, and evacuated according to the following schedule:

| Oil Bath Temperature (°C.) |
|---|
| 156–186° - 30 min |
| 186–200° - 25 min |
| 200–202° - 1 h 5 min |
| 202–250° - 7 min |
| 250–270°- 28 min - stirred |
| 270° - 1 h 50 min - evacuated with oil pump |

The reactor was allowed to cool under vacuum and 4.7 g of polymer was isolated. After being ground in a Wiley mill sufficient to pass through a 40 mesh screen, the polymer was then dried at 200° C. for about 16 hours in a vacuum oven. Inherent viscosity was 0.51. The polyester, when heated between crossed polarizers on a hot stage microscope flowed at 278° C.; TOT was positive. Elemental analysis was consistent with the composition of p-phenylene phenylterephthalate.

B. Polyester of Phenylterephthalic Acid and Hydroquinone Diacetate

A polyester of phenylterephthalic acid and hydroquinone, having an inherent viscosity of 0.82, was prepared as described in Part A except that 18.0 g of the diacid and 15.44 g of the diacetate were used. This polyester was melt-spun at 300°–350° C. to give filaments. The fiber that was collected at 300° C. had the following properties:

| | |
|---|---|
| Tensile Strength | = 3.02 g/denier (2.67 dN/tex). |
| % Elongation | = 0.97% |
| Initial Modulus | = 309 g/denier (273 dN/tex). |

A sample of this fiber was heated in a nitrogen atmosphere according to the following schedule:

| | Time |
|---|---|
| Room Temp. to 230° C. | 10–15 min |
| 230° C. | 2 h |
| 250° C. | 2 h |
| 270° C. | 2 h |
| 290° C. | 10 h |

This heat treatment caused a dramatic increase in the tensile strength:

| | |
|---|---|
| Tensile Strength | = 10.0 g/denier (8.83 dN/tex). |
| % Elongation | = 3.14% |
| Initial Modulus | = 352 g/denier (311 dN/tex). |

C. Comparison of a Phenylterephthalic Acid/Hydroquinone Polyester with the Polyester from Terephthalic Acid and Phenylhydroquinone The polyester from Part B, having the structure

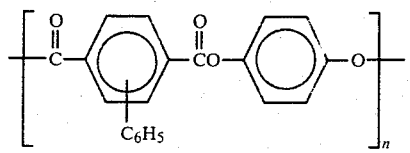

I and an inherent viscosity of 0.82, was compared in melting and filament-forming behavior with an isomeric polyester having the structure

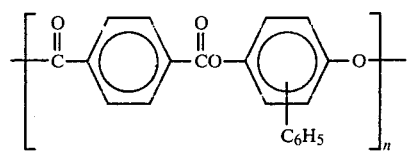

II and an inherent viscosity of 0.72, prepared by essentially the procedure of Part A except that 6.17 g of terephthalic acid and 10.04 g of phenylhydroquinone diacetate were used in place of the starting materials given therein.

Samples of polyesters I and II were examined on a metal block fitted with a thermometer and heated with a small gas burner; the following phenomena were observed:

| I ($\eta_{inh}$ = 0.82) | | II ($\eta_{inh}$ = 0.72) | |
|---|---|---|---|
| 180° | Polymer sticking to block | 210° | Slight sticking to block if polymer is pressed |
| 285° | First filaments could be manually drawn | 325° | First filaments could be manually drawn |
| 293° | Long filaments could be drawn | 335° | Long filaments could be drawn and polymer is essentially melted |
| 300° | Polymer is essentially melted | | |

These tests on polymers of comparable viscosities show that the polyester from phenylterephthalic acid and hydroquinone unexpectedly melts and gives fibers at considerably lower temperatures than the polymer from terephthalic acid and phenylhydroquinone.

EXAMPLE 2

Polyester of Phenylterephthalic Acid and a 4:1 Mixture of Hydroquinone Diacetate and Resorcinol Diacetate

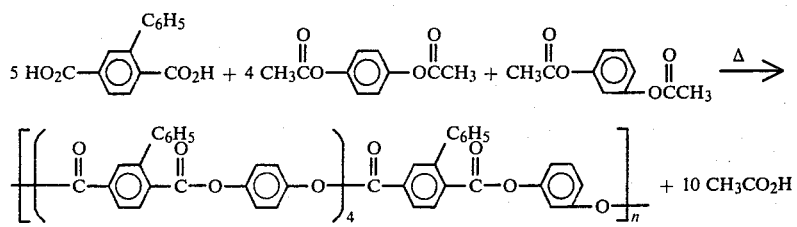

Using the procedure described in Example 1, a mixture of 18.00 g of phenylterephthalic acid, 11.54 g of hydroquinone diacetate and 2.89 g of resorcinol diacetate was heated in an oil bath, stirred and evacuated according to the following schedule:

| Oil Bath Temperature (°C.) |
|---|
| 226–218° - 1 h 16 min |
| 218–255° - 40 min |
| 255–258° - 30 min - stirred |
| 258–264° - 2 h 35 min |
| 264–250° - 15 h 24 min |
| 250–278° - 56 min |

| Oil Bath Temperature (°C.) |
| --- |
| 278–274° - 7 h 5 min evacuated at 0.10 mm |

After work-up as described in Example 1A, 16.1 g of polyester with an inherent viscosity of 0.35 was obtained. When heated between crossed polarizers on a hot stage microscope, the polyester was observed to flow at 212° and TOT was positive. Tests on a heated metal block showed that: (1) the polymer began to stick to the block at about 170°; (2) fibers could be manually drawn beginning about 215°; (3) the polymer was essentially melted at about 275°.

EXAMPLE 3

Polyester of a 1:1 Mixture of Phenylterephthalic Acid and Terephthalic Acid with Hydroquinone Diacetate

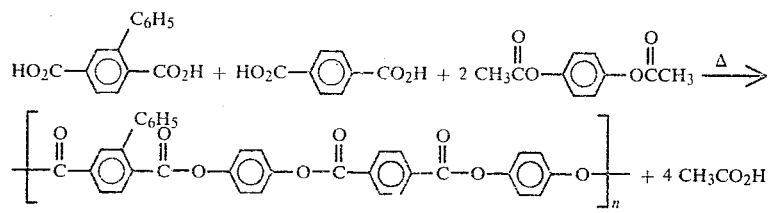

Using the procedure described in Example 1, a mixture of 9.00 g of phenylterephthalic acid, 6.17 g of terephthalic acid, and 14.43 g of hydroquinone diacetate was heated in an oil bath, stirred and evacuated according to the following schedule:

| Oil Bath Temperature (°C.) | |
| --- | --- |
| 228–224° | - min |
| 224° | - 17 min - stirred |
| 224–248° | - 1 h 9 min |
| 248–252° | - 18 h 45 min |
| 252–280° | - 1 h 20 min |
| 280–300° | - 7 h 25 min - evacuated at 0.05–0.10 mm |

After work-up as described in Example 1A, there was obtained 14.7 g of polymer. When heated between crossed polarizers on a hot stage microscope, the polyester was observed to flow at about 347° and TOT was positive. The polymer was not soluble in hexafluoroisopropanol. Tests on a heated metal block showed that: (1) the polymer began to stick to the block at 270°; (2) fibers could be manually drawn beginning at about 350°; (3) the polymer was essentially melted at 370°.

EXAMPLE 4

Polyester of a 3:1 Mixture of Phenylterephthalic and Terephthalic Acids with Hydroquinone Diacetate

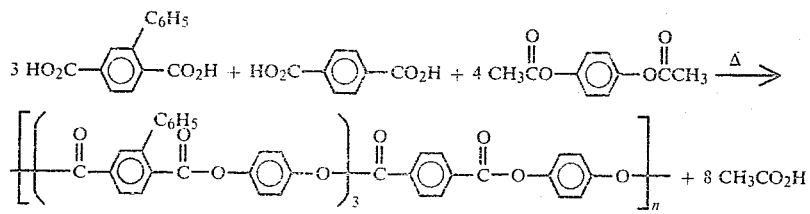

Using the procedure described in Example 1, a mixture of 13.50 g of phenylterephthalic acid, 3.09 g of terephthalic acid and 14.43 g of hydroquinone diacetate was heated in an oil bath, stirred and evacuated according to the following schedule:

| Oil Bath Temperature (°C.) | |
| --- | --- |
| 232–245° | - 1 h 27 min |
| 245–256° | - 30 min - stirred |
| 256–270° | - 1 h 34 min |
| 270–274° | - 18 h 14 min |
| 274–270° | - 5 h 55 min - evacuated at 0.05–0.10 mm |

After work-up as described in Example 1A, there was obtained 17.7 g of polymer with an inherent viscosity of 1.46 (1:1 chloroform-hexafluoroisopropanol). When this polymer was heated between crossed polarizers on a hot stage microscope, it was observed to flow at 291° and TOT was positive. Tests on a heated metal block showed that: (1) the polymer began to stick to the block at about 220°; (2) fibers could be manually drawn beginning at about 270°; (3) the polymer was essentially melted at 315°.

EXAMPLE 5

Polyester of Phenylterephthalic Acid and 2,6-Diacetoxynaphthalene

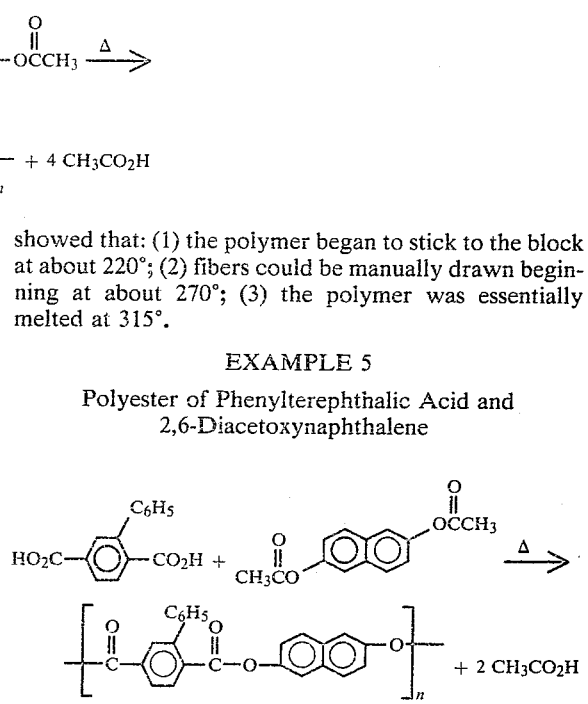

Using the procedure described in Example 1, a mixture of 12.00 g of phenylterephthalic acid and 12.10 g of 2,6-diacetoxynaphthalene was heated in an oil bath, stirred and evacuated according to the following schedule:

| Oil Bath Temperature (°C.) | |
| --- | --- |
| 224–208° | - 1 h 37 min |
| 208–240° | - 27 min |

| Oil Bath Temperature (°C.) | -continued |
| --- | --- |
| 240–252° | - 50 min - stirred |
| 252–260–254° | - 17 h 53 min |
| 254–260–250° | - 7 h 54 min - evacuated at 0.05–0.10 mm stirred during 4 min of this period. |

After work-up as described in Example 1, there was obtained 12.7 g of polymer with an inherent viscosity of 0.35 (1:1 chloroform:hexafluoroisopropanol). When this polymer was heated between crossed polarizers on a hot stage microscope, it was observed to flow at 184°, and TOT was positive. Tests on a heated metal block showed that: (1) the polymer began to stick to the block at about 160°; (2) fibers could be manually drawn beginning at about 180°; (3) the polymer was essentially melted at 210°.

EXAMPLE 6

Polyester of Phenylterephthalic Acid and 4,4′-Diacetoxybiphenyl

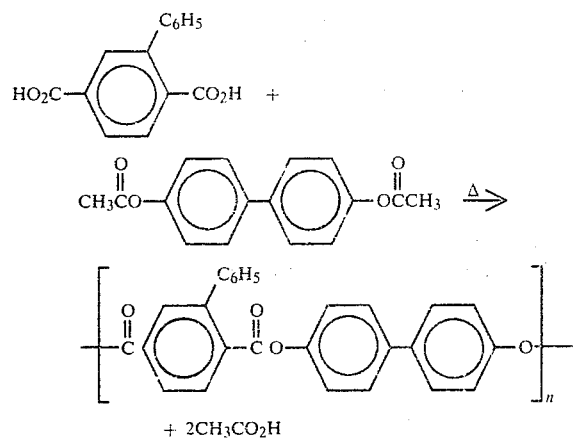

Using the procedure described in Example 1A, a mixture of 12.00 g of phenylterephthalic acid and 13.39 g of 4,4′-diacetoxybiphenyl was heated in an oil bath, stirred and evacuated according to the following schedule:

| Oil Bath Temperature (°C.) | |
| --- | --- |
| 224–220° | - 2 h 2 min |
| 220–248° | - 16 min |
| 248–250° | - 47 min - stirred |
| 250–245° | - 17 h 34 min |
| 245–276° | - 2.25 h |
| 276–267° | - 6.25 h - evacuated at 0.05–0.10 mm |

After work-up as described in Example 1A, there was obtained 16.4 g of polymer with an inherent viscosity of 0.99. When this polymer was heated between crossed polarizers on a hot stage microscope, it was observed to flow at 240°, and TOT was positive. Tests on a heated metal block showed that: (1) the polymer began to stick to the block at about 175°; (2) fibers could be manually drawn beginning about 255°; (3) the polymer was essentially melted at about 270°. This polyester was melt-spun at 276° to give lustrous filaments.

EXAMPLE 17

Polyester of Phenylterephthalic Acid and 1,4-DiacetoxyNaphthalene

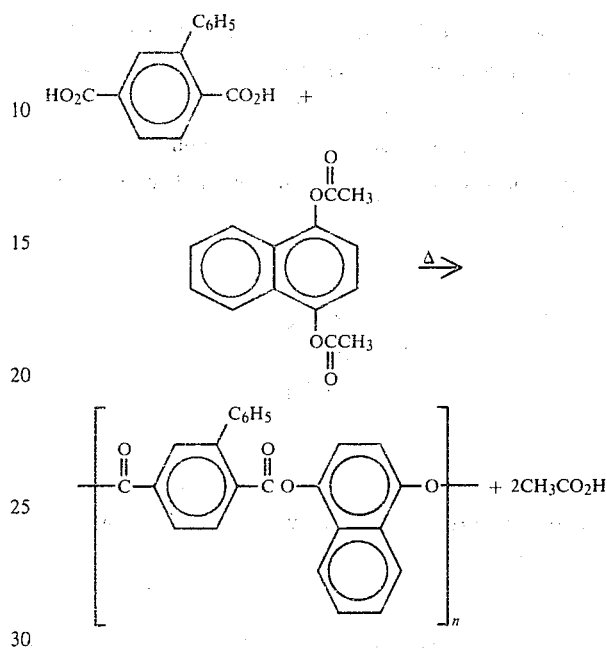

Using the procedure described in Example 1, a mixture of 12.00 g of phenylterephthalic acid and 12.83 g of 1,4-diacetoxynaphthalene was heated in an oil bath, stirred and evacuated according to the following schedule:

| Oil Bath Temperature (°C.) | |
| --- | --- |
| 224–236° | - 1 h 32 min |
| 236–244° | - 44 min |
| 244–234° | - 16 h 34 min |
| 234–254° | - 7.5 h - evacuated at 0.10 mm |

After work-up as described in Example 1A, there was obtained 11.0 g of polymer with an inherent viscosity of 0.38 (1:1 chloroform:hexafluoroisopropanol). When this polymer was heated between crossed polarizers on a hot stage microscope, it was observed to flow at 210°, and TOT was positive. Tests on a heated metal block showed that: (1) the polymer began to stick to the block at about 170°; (2) fibers could be manually drawn beginning about 200°; (3) the polymer was essentially melted at about 230°.

I claim:

1. A fiber forming melt-spinnable (co)polyester consisting essentially of units having the structural formulas

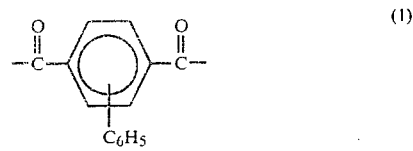

(1)

or a combination of (1) and up to 50 mol % of

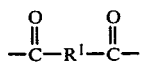 (2)

wherein $R^1$ is 1,4-phenylene, 2,6-naphthalene, 4,4'-biphenylene or mixtures thereof, and (3) —O—$R^2$—O— wherein $R^2$ is 1,4-phenylene, 2,6-napthalene, 1,4-naphthalene, 4,4'-biphenylene or mixtures thereof or a combination of (3) with up to 20 mol % of

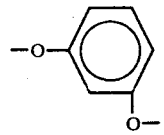

based on the total mols of dioxy units present.

2. A (co)polyester according to claim 1 consisting essentially of units having the structural formulas

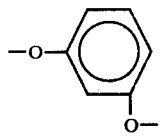

wherein $R^2$ is 1,4-phenylene, 2,6-naphthalene, 1,4-naphthalene, 4,4'-biphenylene or mixtures thereof.

3. A (co)polyester according to claim 2 wherein $R^2$ is

4. A (co)polyester according to claim 1 consisting essentially of units having the structural formulas

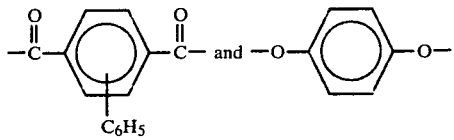

and
with up to 20 mol % of

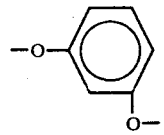

based on the total mols of dioxy units present.

5. A (co)polyester according to claim 1 consisting essentially of units having the structural formulas

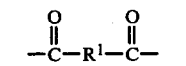 (1)

and up to 50 mol % of

 (2)

wherein $R^1$ is 1,4-phenylene, 2,6-naphthalene, 4,4'-biphenylene, or mixtures thereof and

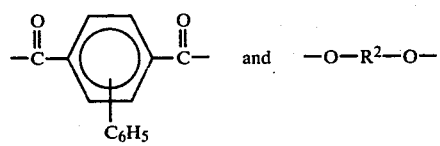 (3)

6. A polyester according to claim 5 wherein $R^1$ is

7. A filament of the (co)polyester of claim 1.

* * * * *

UNITED STATES PATENT AND TRADEMARK OFFICE
CERTIFICATE OF CORRECTION

PATENT NO. : 4,294,955
DATED : Oct. 13, 1981
INVENTOR(S) : John F. Harris, Jr.

It is certified that error appears in the above—identified patent and that said Letters Patent is hereby corrected as shown below:

Column 12, line 8, delete "and".

*Signed and Sealed this*

*Nineteenth* Day of *January 1982*

[SEAL]

*Attest:*

GERALD J. MOSSINGHOFF

*Attesting Officer* — *Commissioner of Patents and Trademarks*

UNITED STATES PATENT AND TRADEMARK OFFICE
CERTIFICATE OF CORRECTION

PATENT NO. : 4,294,955
DATED : Oct. 13, 1981
INVENTOR(S) : John F. Harris, Jr.

It is certified that error appears in the above—identified patent and that said Letters Patent is hereby corrected as shown below:

Column 7, about line 35, change "228-224° - min" to read -- 228-224° - 26 min --.

Column 10, line 1, change "Example 17" to read -- Example 7 --.

Signed and Sealed this

Twenty-third Day of February 1982

[SEAL]

Attest:

GERALD J. MOSSINGHOFF

Attesting Officer    Commissioner of Patents and Trademarks